US00PP24516P2

(12) United States Plant Patent
Wicki-Freidl

(10) Patent No.: US PP24,516 P2
(45) Date of Patent: Jun. 3, 2014

(54) ***LOBULARIA* PLANT NAMED 'INLBUBLUPR'**

(50) Latin Name: *(Lobularia canariensis×Lobularia maritima)×Lobularia maritima*
Varietal Denomination: Inlbublupr

(75) Inventor: Peter Wicki-Freidl, Canary Islands (ES)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 46 days.

(21) Appl. No.: 13/573,173

(22) Filed: Aug. 27, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — C. A. Whealy

(57) ABSTRACT

A new and distinct cultivar of *Lobularia* plant named 'Inlbublupr', characterized by its outwardly spreading, mounding and trailing to decumbent plant habit; freely branching habit; vigorous growth habit; relatively long leaves; freely and continuous flowering habit; relatively long flowering period; white-colored small flowers that with development become light violet in color; and tolerance to high temperatures.

1 Drawing Sheet

Botanical designation: (*Lobularia canariensis*×*Lobularia maritima*)×*Lobularia maritima.*
Cultivar denomination: 'INLBUBLUPR'.

BACKGROUND OF THE INVENTION

The present invention relates to a new and distinct cultivar of *Lobularia* plant, botanically known as (*Lobularia canariensis*×*Lobularia maritima*)×*Lobularia maritima* and hereinafter referred to by the name 'Inlbublupr'.

The new *Lobularia* plant is a product of a planned breeding program conducted by the Inventor in La Palma, Canary Islands, Spain. The objective of the breeding program was to develop new *Lobularia* plants with unique and attractive flower coloration.

The new *Lobularia* plant originated from a cross-pollination conducted by the Inventor in March, 2009 in La Palma, Canary Islands, Spain of a *Lobularia canariensis*×*Lobularia maritima* 'Inlbusnopr', disclosed in U.S. Plant Pat. No. 21,594, as the female, or seed, parent, with an unnamed selection of *Lobularia maritima*, not patented, as the male, or pollen, parent. The new *Lobularia* plant was discovered and selected by the Inventor as a single flowering plant within the progeny of the stated cross-pollination in a controlled greenhouse environment in La Palma, Canary Islands, Spain in May, 2010. Asexual reproduction of the new *Lobularia* plant by vegetative cuttings in a controlled greenhouse environment in La Palma, Canary Islands, Spain since November, 2010 has shown that the unique features of this new *Lobularia* plant are stable and reproduced true to type in successive generations.

SUMMARY OF THE INVENTION

Plants of the new *Lobularia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Inlbublupr'. These characteristics in combination distinguish 'Inlbublupr' as a new and distinct *Lobularia* plant:

1. Outwardly spreading, mounding and trailing to decumbent plant habit.
2. Freely branching and vigorous growth habit.
3. Relatively long leaves.
4. Freely and continuous flowering habit.
5. Relatively long flowering period.
6. White-colored small flowers that with development become light violet in color.
7. Good garden performance and tolerant to high temperatures.

Plants of the new *Lobularia* differ from plants of the female parent, 'Inlbusnopr', in the following characteristics:

1. Plants of the new *Lobularia* and 'Inlbusnopr' differ in stem and leaf color.
2. Plants of the new *Lobularia* have smaller flowers than plants of 'Inlbusnopr'.
3. Plants of the new *Lobularia* and 'Inlbusnopr' differ in flower color as plants of 'Inlbusnopr' have white-colored flowers.

Plants of the new *Lobularia* differ from plants of the male parent selection primarily in leaf size as plants of the new *Lobularia* have longer leaves than plants of the male parent selection.

Plants of the new *Lobularia* can be compared to unnamed selections plants of seed-produced *Lobularia maritima*, not patented. In side-by-side comparisons, plants of the new *Lobularia* differed from plants of unnamed selections of seed-produced *Lobularia maritima* in the following characteristics:

1. Plants of the new *Lobularia* were larger and more vigorous than plants of unnamed selections of seed-produced Lobularia maritima.

2. Plants of the new *Lobularia* were more high temperature tolerant than plants of unnamed selections of seed-produced *Lobularia maritima*.

BRIEF DESCRIPTION OF THE PHOTOGRAPHS

The accompanying colored photographs illustrate the overall appearance of the new *Lobularia* plant showing the colors as true as it is reasonably possible to obtain in colored reproductions of this type. Colors in the photographs may differ slightly from the color values cited in the detailed botanical description which accurately describe the colors of the new *Lobularia* plant.

The photograph at the bottom of the sheet comprises a side perspective view of a typical flowering plant of 'Inlbublupr' grown in a container.

The photograph at the top of the sheet is a close-up view of a typical flowering plant of 'Inlbublupr'.

DETAILED BOTANICAL DESCRIPTION

The aforementioned photographs and following observations, measurements and values describe plants grown during the summer in one-gallon containers an outdoor nursery in Bonsall, Calif. under commercial practices typical of commercial *Lobularia* production. During the production of the plants, day temperatures ranged from 20° C. to 29° C. and night temperatures ranged from 14° C. to 18° C. Plants were pinched one time at planting and were six weeks old when the photographs and description were taken. In the following description, color references are made to The Royal Horticultural Society Colour Chart, 2007 Edition, except where general terms of ordinary dictionary significance are used.

Botanical classification: (*Lobularia canariensis*×*Lobularia maritima*)×*Lobularia maritima* 'Inlbublupr'.

Parentage:

*Female, or seed, parent.*—*Lobularia canariensis*×*Lobularia maritima* 'Inlbusnopr', disclosed in U.S. Plant Pat. No. 21,594.

*Male, or pollen, parent.*—Unnamed selection of *Lobularia maritima*, not patented.

Propagation:

*Type.*—Terminal vegetative cuttings.

*Time to initiate roots, summer.*—About four to five days at temperatures of about 18° C. to 24° C.

*Time to initiate roots, winter.*—About five to seven days at temperatures of about 7° C. to 16° C.

*Time to produce a rooted young plant, summer.*—About four weeks at 18° C. to 24° C.

*Time to produce a rooted young plant, winter.*—About six weeks at 7° C. to 16° C.

*Root description.*—Medium in thickness, fibrous; white in color.

*Rooting habit.*—Moderately freely branching; medium density.

Plant description:

*Plant form and growth habit.*—Outwardly spreading, mounding and trailing to decumbent plant habit; freely branching habit with about nine to ten primary lateral branches and numerous secondary and tertiary lateral branches developing per plant; vigorous growth habit.

*Plant height.*—About 22.5 cm.

*Plant diameter* (*area of spread*).—About 53 cm.

*Lateral branches.*—Length: About 27 cm. Diameter: About 2 mm. Internode length: About 2.2 cm. Strength: Strong, tough. Texture: Scattered pubescent; longitudinally ridged. Color: Close to 147B.

Foliage description:

*Arrangement.*—Alternate; simple.

*Length.*—About 6.5 cm.

*Width.*—About 4 mm.

*Shape.*—Lanceolate.

*Apex.*—Acute.

*Base.*—Attenuate.

*Margin.*—Entire.

*Texture, upper and lower surfaces.*—Pubescent.

*Venation pattern.*—Single midvein.

*Color.*—Developing and fully expanded leaves, upper surface: Close to 137B; venation, close to 137B. Developing and fully expanded leaves, lower surface: Close to 146B; venation, close to 146C.

*Petioles.*—Length: About 5 mm. Diameter: About 1 mm. Texture, upper and lower surfaces: Pubescent. Color, upper surface: Close to 146B. Color, lower surface: Close to 146C.

Flower description:

*Flower type and habit.*—Small single rounded flowers arranged in narrow terminal racemes; flowers face mostly outwardly; freely flowering habit, about 50 flowers developing per inflorescence.

*Natural flowering season.*—Relatively long flowering period; plants flower continuously from spring until autumn in southern California.

*Flower longevity on the plant.*—About five days; flowers not persistent.

*Fragrance.*—Faintly fragrant; sweet, vanilla-like.

*Inflorescence height.*—About 11 cm.

*Inflorescence diameter.*—About 2.5 cm.

*Flower diameter.*—About 5 mm.

*Flower depth* (*height*).—About 3 mm.

*Flower buds.*—Length: About 2 mm. Diameter: About 3 mm. Shape: Roughly spherical. Color: Close to NN155D.

*Petals.*—Quantity and arrangement: Four petals arranged in a single whorl. Length: About 4 mm. Width: About 3 mm. Shape: Oval. Apex: Rounded. Base: Attenuate. Margin: Entire. Texture, upper and lower surfaces: Smooth, glabrous; velvety. Color: When opening, upper and lower surfaces: Close to NN155D. Fully opened, upper surface: Close NN155D; with development, color progressively shifts to close to 84D and to 85A to 85B; high light conditions enhance violet color development. Fully opened, lower surface: Close NN155D; with development, color shifts to close to 85B; high light conditions enhance violet color development.

*Sepals.*—Quantity and arrangement: Four sepals arranged in a single whorl; calyx, cup-shaped. Length: About 1.5 mm. Width: About 1 mm. Shape: Elliptical. Apex: Acute. Base: Truncate. Margin: Entire. Texture, upper surface: Smooth, glabrous. Texture, lower surface: Pubescent. Color, upper surface: Close to 146A. Color, lower surface: Close to 146B.

*Peduncles.*—Length: About 2.4 cm. Width: About 2 mm. Strength: Strong. Texture: Pubescent. Color: Close to 146B.

*Pedicels.*—Length: About 1.2 mm. Width: Less than 1 mm. Strength: Moderately strong. Texture: Scattered pubescence. Color: Close to 146B.

*Reproductive organs*.—Stamens: Quantity per flower: Six. Filament length: About 1.5 mm. Filament color: Close to 145D. Anther shape: Oval. Anther length: Less than 1 mm. Anther color: Close to 161A. Pollen amount: Scarce. Pollen color: Close to 163C. Pistils: Quantity per flower: One. Pistil length: About 2 mm. Style length: Less than 1 mm. Style color: Close to 137D. Stigma shape: Rounded. Stigma color: Close to 145B. Ovary color: Close to 137D.

*Seeds and fruits*.—Seed and fruit production have not been observed on plants of the new *Lobularia*.

Pathogen & pest resistance: Plants of the new *Lobularia* have not been noted to be resistant to pathogens or pests common to *Lobularia* plants.

Garden performance: Plants of the new *Lobularia* have been observed to have good garden performance; have been noted to tolerate temperatures from about −4° C. to about 32° C. and to have excellent tolerance to rain and wind.

It is claimed:

1. A new and distinct *Lobularia* plant named 'Inlbublupr' as illustrated and described.

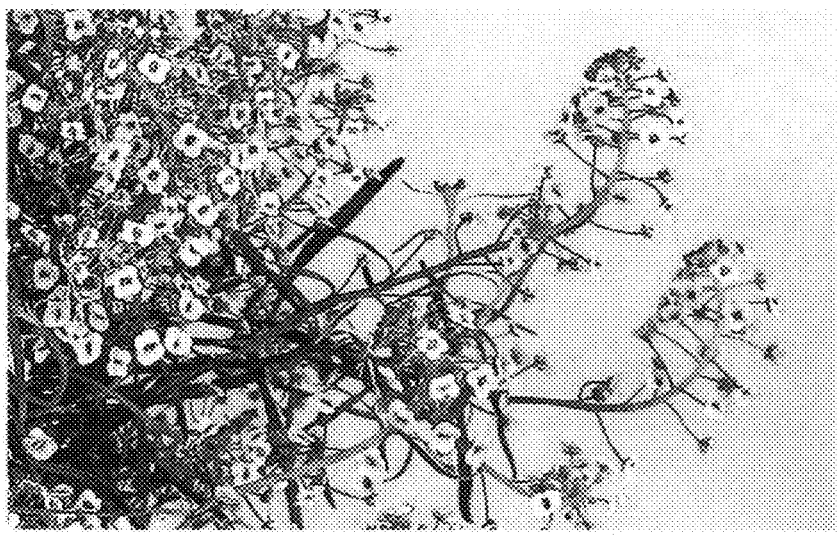
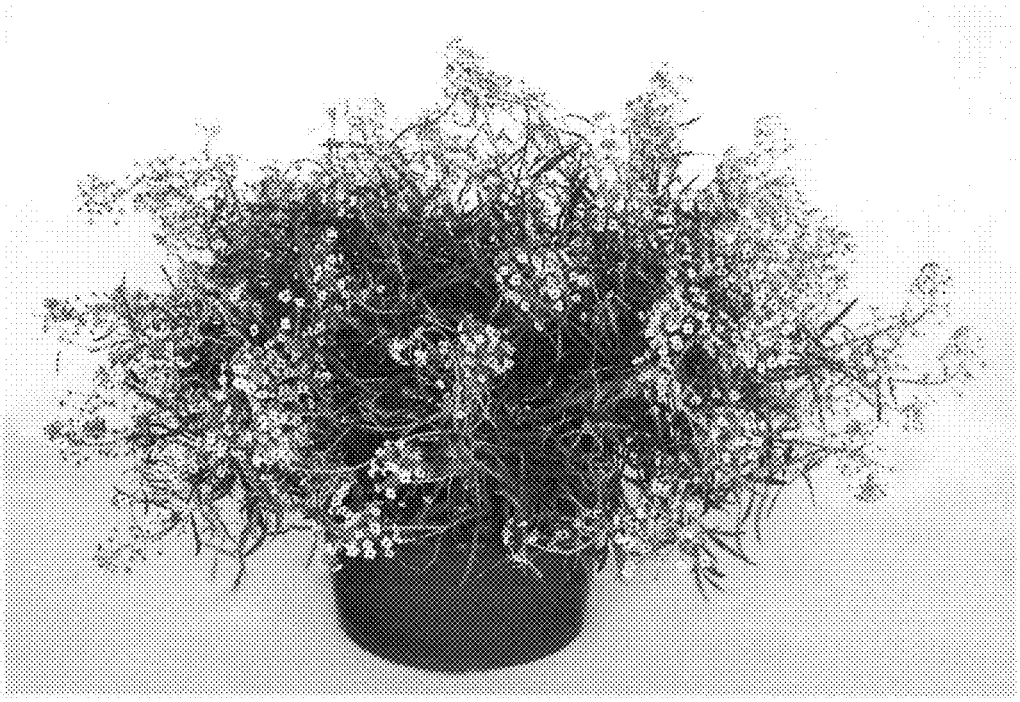

* * * * *